United States Patent [19]

Rutherford

[11] Patent Number: 5,149,691
[45] Date of Patent: Sep. 22, 1992

[54] ISSUE REPAIR AND REGENERATION THROUGH THE USE OF PLATELET DERIVED GROWTH FACTOR (PDGF) IN COMBINATION WITH DEXAMETHASONE

[75] Inventor: Robert B. Rutherford, Farmington, Conn.

[73] Assignee: Creative BioMolecules, Inc., Hopkinton, Mass.

[21] Appl. No.: 669,070

[22] Filed: Mar. 12, 1991

[51] Int. Cl.$^5$ ............................................. A61K 37/36
[52] U.S. Cl. ........................................ 514/12; 514/2; 514/21; 514/8
[58] Field of Search ................................ 514/12, 21, 8

[56] References Cited

PUBLICATIONS

J. of Biol. Chem. vol. 260, No. 13, (1985), pp. 8056–8063, Levenson et al.
Proc. Soc. Exp. Biol. Med. 158, 292–297 (1978), Cheung et al.

Primary Examiner—Howard E. Schain
Attorney, Agent, or Firm—Testa, Hurwitz & Thibeault

[57] ABSTRACT

Disclosed is a method for the regeneration of tissue, the treatment of external wounds and the treatment of periodontal disease comprised of applying to the afflicted tissue a pharmaceutically effective amount of a composition comprised of platelet-derived growth factor and dexamethasone.

11 Claims, 6 Drawing Sheets

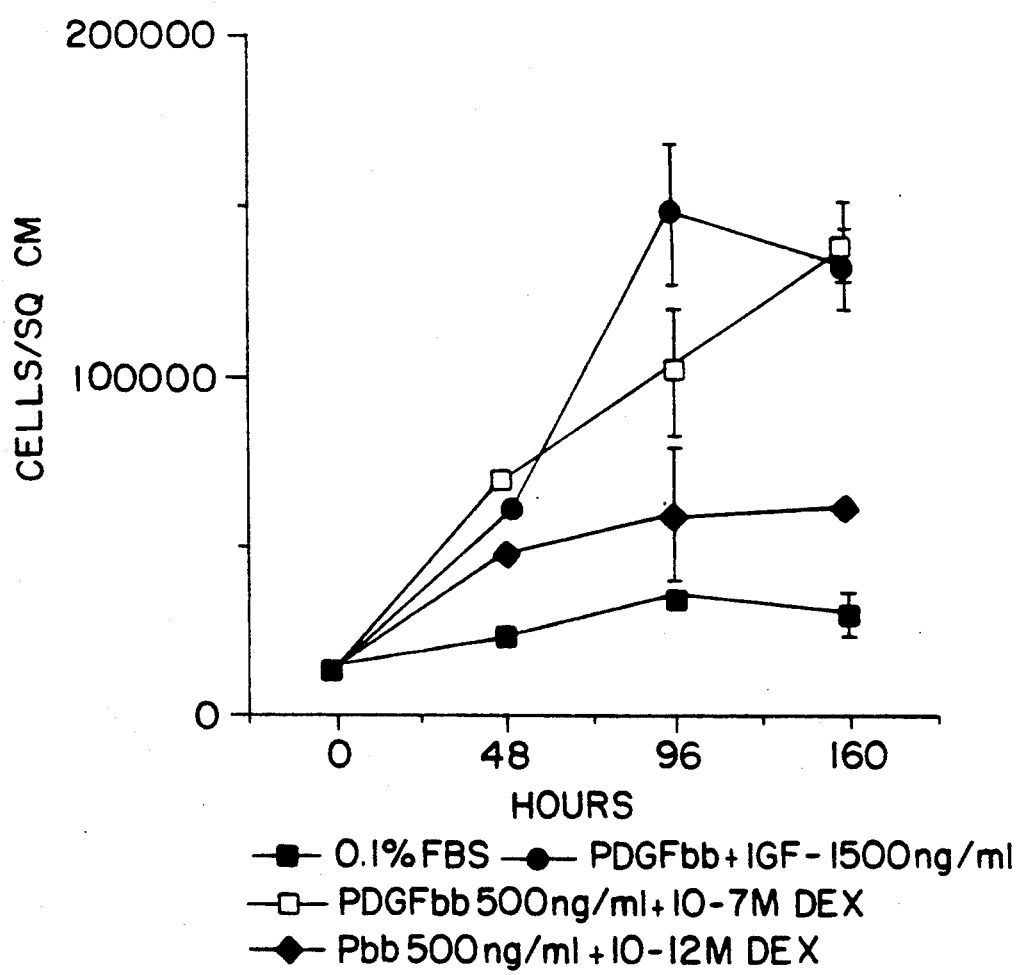

TISSUE REPAIR AND REGENERATION THROUGH THE USE OF PLATELET DERIVED GROWTH FACTOR (PDGF) IN COMBINATION WITH DEXAMETHASONE

FIELD OF THE INVENTION

The present invention lies in the field of tissue regeneration and wound regeneration and wound repair.

BACKGROUND OF THE INVENTION

Polypeptide growth factors are a class of natural biological mediators that regulate the proliferation, differentiation, motility and matrix synthesis of nearly all cell types. These properties, demonstrable in vitro, have led to the proposal that such factors play important roles in soft and hard tissue repair. Platelet-derived growth factor (PDGF) is a very well characterized example of such a polypeptide growth factor.

PDGF is a peptide hormone produced by blood platelets which influences the regulation of a broad array of biological systems including wound repair, arteriosclerosis, neoplasia, embryogenesis and bone marrow fibrosis. PDGF is a mitogen which is a substance which induces mitosis of cells and thus cellular proliferation. In wound repair, PDGF elicits both chemotaxis and mitogenic responses (i.e., induces mitosis) in fibroblasts, smooth muscle, glial cells, etc. Injury to the endothelium lining the vessel wall is believed to cause platelets to adhere to exposed connective tissue at the wound site, with the concomitant release of PDGF. The released PDGF is thought to chemotactically recruit many cell types including fibroblasts, monocytes, glial and smooth muscle to migrate in to the site of the wound. PDGF is also believed to stimulate DNA synthesis and proliferation of these cells thereby increasing their numbers of the site of the wound. Increased cellular proliferation thus leads to accelerated tissue regeneration and wound repair.

The mitogenic property of PDGF has been augmented by the addition of insulin-like growth factor-1 (IGF-1), Antoniades et al., U.S. Pat. No. 4,861,757 and transforming growth factor alpha (TGF-$\alpha$), Antoniades et al., U.S. Pat. No. 4,874,746. Levenson et al. (1985) J. Biol. Chem 260:8056–63 showed that the synthetic glucocorticoid, dexamethasone, acts synergistically with cartilage-derived growth factor (CDGF) to enhance the stimulation of DNA synthesis in quiescent Swiss 3T3 cells, approximately doubling DNA synthesis while having a neutral effect when added with PDGF. In addition, they presented data showing that the simultaneous addition of dexamethasone to PDGF stimulated cultures had no effect on DNA synthesis over that observed with PDGF alone.

SUMMARY OF THE INVENTION

We have discovered that, contrary to the data of the prior art, that dexamethasone synergistically enhances the mitogenic effect of PDGF on cells.

Accordingly, the present invention is comprised of promoting the proliferation of mammalian cells by treating the cells with a composition that includes PDGF and dexamethasone.

Another aspect of the present invention is comprised of healing a wound in an animal, e.g., a human patient, by applying to the wound a therapeutically effective amount of a composition that includes PDGF and dexamethasone.

Another aspect of the present invention is comprised of treating connective tissue and bone of mammals with a composition of PDGF and dexamethasone to repair and regenerate said bone and connective tissue.

Still another aspect of the present invention is a method for treating periodontal disease comprised of applying a composition of PDGF and dexamethasone to the affected gum tissue and periodontal ligament.

Other features and advantages of the present invention will be apparent from the following description of the preferred embodiments thereof.

BRIEF DESCRIPTION OF THE DRAWINGS

FIGS. 3A and 3B graphically illustrates the data from Example 2 showing that the mitogenic activity of PDGF changes as a function of the concentration of dexamethasone using PDGF+IGF-1 as a control reference.

DETAILED DESCRIPTION OF THE INVENTION

Figure 1:
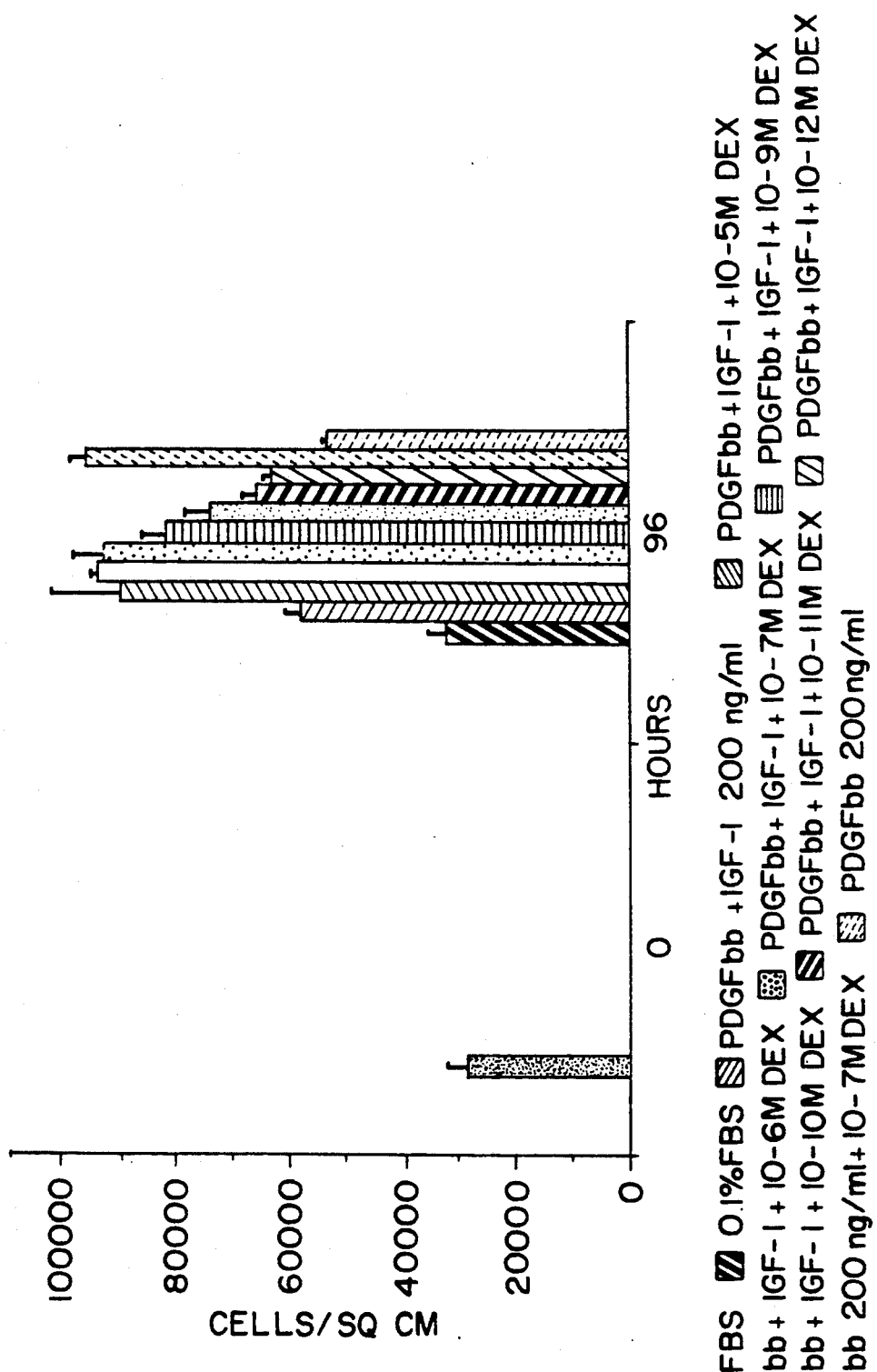
FIG. 1 is a graphic representation of the data obtained from Example 1 showing that dexamethasone influences the mitogenic activity of both PDGF alone and PDGF+IGF-1.

External wounds, for example, skin ulcers, periodontal disease, burns, lesions and the like, are healed, and bone connective tissue regenerated, according to the present invention, by treatment with compositions that includes PDGF and dexamethasone.

Native PDGF is a dimeric molecule comprised of two polypeptide chains, one or more of which may be glycosylated. The two chains [referred to as alpha ($\alpha$), and beta ($\beta$)] are homologous but not identical. They have molecular weights of about 17,000 or 18,000 and about 13,000 to 14,000, respectively. In vivo, the $\alpha$ and $\beta$ chains are synthesized from larger precursor molecules which are subsequently processed at the amino and carboxyltermini. The mature human $\alpha$ chain is comprised of 110 or 125 amino acids and various N-linked sugar side chains, the length and amino acid sequence being dependent in a small 1 on the tissue source. The fully processed human $\beta$ chain is encoded by the c-sis gene and is comprised of 112 amino acids.

Biologically active PDGF can exist as homodimer or heterodimer, i.e. $\alpha\alpha$, $\beta\beta$ and $\alpha\beta$. The molecular weights of $\alpha\alpha$ homodimer and $\beta\beta$ homodimer are about 35,000 or about 32,000, respectively.

Presently, several methods are known by which PDGF can be extracted from human platelets. See for example, Heidin et al. (1979) Proc. Natl. Acad. Sci. USA 76:3722–3726; Antoniades et al. (1979) Proc. Natl. Acad. Sci. USA 76:1809–1813; Antoniades et al., U.S. Pat. No. 4,479,896; Lipton et al., U.S. Pat. No. 4,350,687. In addition, PDGF can be produced recombinantly using either transformed eukaryotic cells, such as yeast, see EP Publication No. 0177957, or in procaryotic cells such as E. coli, see Charette et al., filed Feb. 11, 1988. PDGF is also commercially available from Amgen Corporation, Thousand Oaks, Calif.; PDGF Inc., Boston, Mass.; Collaborative Research Inc., Waltham, Mass.; and Creative BioMolecules, Inc., Hopkinton, Mass.

According to the present invention, PDGF refers to naturally occurring PDGF, PDGF obtained by recombinant means expressed by either eukaryotic or bacterial host cells, biologically active mutant forms of PDGF, biologically active fragments of PDGF and biologically active mutants of biologically active fragments of PDGF.

Dexamethasone is commercially available from a number of sources, for example Sigma Chemical Co., Saint Louis, Mo.

Treatment of Wounds and Periodontal Disease

The healing of external wounds and periodontal disease afflicted tissue can be promoted by directly applying a composition of PDGF and dexamethasone in a pharmaceutically acceptable medium such as a biocompatible gel to the affected tissue. The tissue can be external tissue, internal tissue, gum tissue or periodontal ligature afflicted with periodontal disease.

The range of concentration can be 10 mg/ml to 1 $\mu$g/ml PDGF and 3.92 mg/3.92 $\mu$g/ml dexamethasone.

Other growth factors such as transforming growth factor-$\alpha$ (TGF-$\alpha$) and insulin-like growth factors (IGF-1) can be further added to the PDGF and dexamethasone composition to further promote healing of the injured tissue.

If TGF-$\alpha$ or IGF-1 is added to the PDGF-dexamethasone mixture, they can be combined in a weight-to-weight ratio of PDGF to TGF-$\alpha$ or IGF-1 of 1:4 and 25:1, preferably between 1:2 and 10:1 and more preferably 1:1 or 2:1.

In preferred embodiments of both aspects of the present invention, the composition of PDGF and dexamethasone is prepared by combining in a pharmaceutically acceptable carrier substance for topical administration. Examples of pharmaceutically acceptable carriers are commercially available inert gels or liquids (e.g., saline supplemented with albumin or methyl cellulose). Typical of such formulations are ointments, creams and gels. Also, for certain tissues a collagen matrix can be used.

Ointments generally are prepared using either (1) an oleaginous base, i.e. one containing fixed oils or hydrocarbons, such as white petrolatum or mineral oil, or (2) an absorbent base, i.e. one consisting of an anhydrous substance or substances which can absorb water, for example, anhydrous lanolin. Customarily, following formation of the base, whether oleaginous or absorbent, the active ingredients PDGF and dexamethasone are added in an amount affording the desired concentration.

Creams are oil/water emulsions. They are comprised of an oil phase (internal phase) containing typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauri sulfate; hydrophilic colloids, such as acacia colloidal clays, veegum, and the like. Upon formation of the emulsion, the active ingredients PDGF and dexamethasone are added in an amount to achieve the desired concentration.

Gels are comprised of a base selected from an oleaginous base, water, or an emulsion-suspension base, as the one previously described. To the base is added a gelling agent which forms a matrix in the base, increasing its viscosity. Examples of gelling agents are hydroxypropyl cellulose, acrylic acid polymers, and the like. Customarily, the active ingredients PDGF and dexamethasone are added to the formulation at the desired concentration at a point preceding addition of the gelling agent.

The amounts of PDGF and dexamethasone incorporated into the formulation of the present invention is not critical; the concentration should only be in a range sufficient to permit ready application of the formulation to the wound area in an amount which will deliver the desired amount of PDGF and dexamethasone. A typical gel formulation useful for the topical administration of PDGF and dexamethasone is composed of the following:

|  | % by Weight |
| --- | --- |
| sterile distilled water | 92.38 |
| sodium dibasic phosphate | 0.03 |
| Carbapol TM | 0.5 |
| glycerin | 1.6 |
| m-cresol | 0.25 |
| sodium hydroxide (1N) | 0.5 |

In addition, if the tissue which is to be regenerated is bone or cartilage, a suitable pharmaceutical carrier is a bone collagen matrix produced as described in U.S. Pat. No. 4,975,526, Kuberasampath et al. The collagen matrix is a biodegradable, biocompatible mineral-free, insoluble Type-I bone collagen particles being depleted of non-collagenous protein. The collagen matrix particles have a mean diameter within the range of 70 $\mu$m-850 $\mu$m, and having an increased intraparticle surface area relative to untreated material. PDGF and dexamethasone are first dissolved in a suitable solvent such as buffered sterile saline solution and then added to the collagen matrix. The mixture is vortexed many times. The matrix can then be lyophilized and shaped as desired or implanted into an area of bone or cartilage by packing.

Other useful matrix materials are homopolymers and copolymers of glycolic acid and lactic acid, hydroxyapatite, tricalcium and other calcium phosphates, and particulate, demineralized, guanidine extracted, species-specific(allogenic) bone. The matrix containing the PDGF and dexamethasone can then be applied into a shape spanning the bone or cartilage defect to serve as a "temporary scaffold" and substratum for recruitment of migratory progenitor cells and as a base for their subsequent anchoring and proliferation.

Having generally described the present invention, the invention will be more readily understood by the following specific examples which are included for purposes of illustration and are not intended to be limited unless otherwise specified.

EXAMPLE 1

Potentiation of mitogenic effect of PDGF, IGF-1 or PDGF and IGF-1 by Dexamethasone The present experiments were all performed on low passage, human diploid fibroblasts obtained from the periodontal ligaments and dental pulps of extracted teeth. The cells were cultured under standard culture conditions and stocks were propagated with 10% fetal bovine serum (FBS). For the experiments detailed here, the cells were plated at 10,000 to 15,000 cells per 1.88 cm² of surface area in 24 well culture plates and conditioned in medium containing 0.1% FBS for 24-48 hours prior to treatment. The cells were then exposed once to the indicated concentrations of PDGF and dexamethasone in culture media at time zero. The cells were quantitatively harvested from each well and the total cell population densities were determined using a Coulter counter. The PDGF-$\beta\beta$ and -$\alpha\alpha$ used in these studies were a recombinant human analog of PDGF produced in *E. coli* which was provided by Creative BioMolecules, Hopkinton, Mass. The dexamethasone was purchased from Sigma Chemical Company, St. Louis, Mo.

Cell cultures in 24-well plates as prepared described above were treated with the following materials and the extent of cell growth determined.

Plate 1 contained 0.1% FBS
Plate 2 contained 0.1% FBS
Plate 3 contained PDGF-$\beta\beta$ 200 ng/ml+IGF-1 200 ng/ml
Plate 4 contained PDGF-$\beta\beta$ 200 ng/ml+IGF-1 200 ng/ml+$10^{-5}$M Dexamethasone
Plate 5 contained PDGF-$\beta\beta$ 200 ng/ml+IGF-1 200 ng/ml+$10^{-6}$M Dexamethasone
Plate 6 contained PDGF-$\beta\beta$ 200 ng/ml+IGF-1 200 ng/ml+$10^{-7}$M Dexamethasone
Plate 7 contained PDGF-$\beta\beta$ 200 ng/ml+IGF-1 200 ng/ml+$10^{-9}$M Dexamethasone
Plate 8 contained PDGF-$\beta\beta$ 200 ng/ml+IGF-1 200 ng/ml+$10^{-10}$M Dexamethasone
Plate 9 contained PDGF-$\beta\beta$ 200 ng/ml+IGF-1 200 ng/ml+$10^{-11}$M Dexamethasone
Plate 10 contained PDGF-$\beta\beta$ 200 ng/ml+IGF-1 200 ng/ml+$10^{-12}$M Dexamethasone
Plate 11 contained PDGF-$\beta\beta$ 200 ng/ml+$10^{-7}$M Dexamethasone
Plate 12 contained PDGF-$\beta\beta$ 200 ng/ml All of the plates except for plate 1 were incubated for 96 hours. Plate 1 was incubated for 30 minutes.

Figure 2:
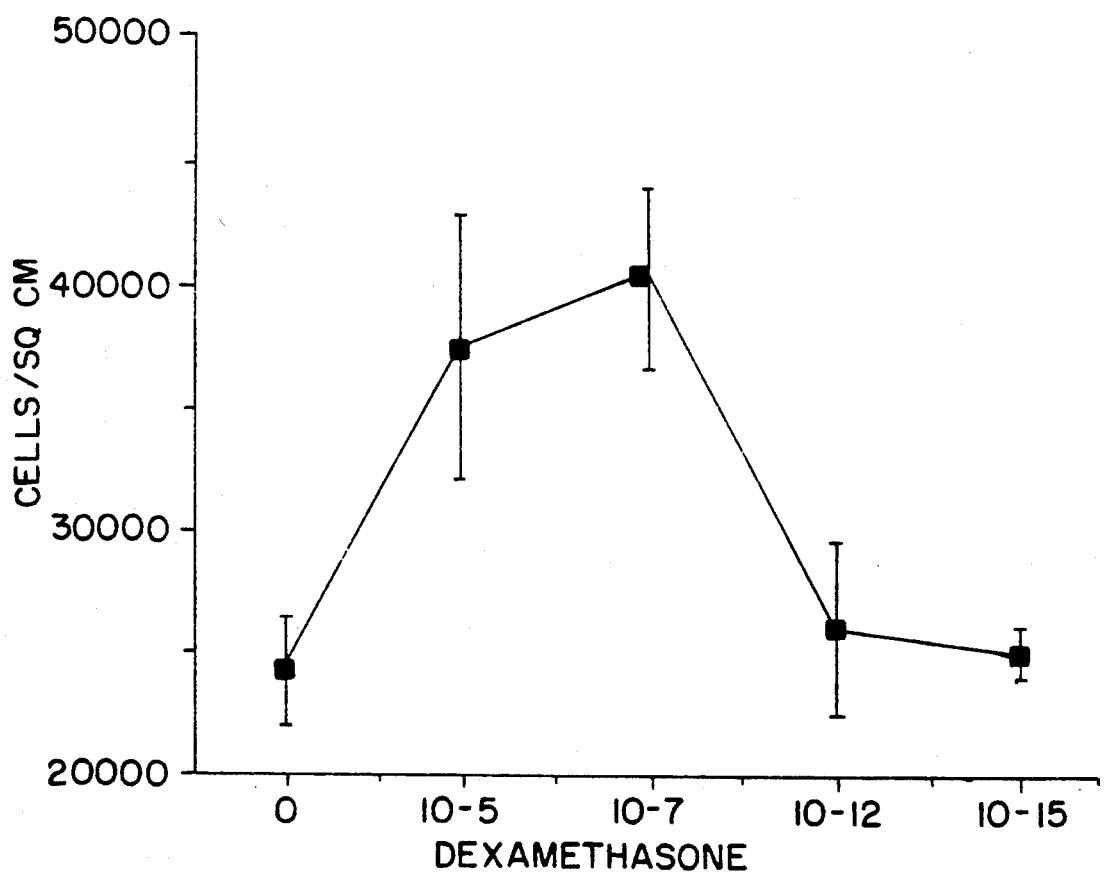
FIG. 2 illustrates the data obtained in Example 1 showing the effect that differing concentrations of dexamethasone has on the mitogenic activity of PDGF+IGF-1.

The data are illustrated in FIGS. 1-2 and are the mean standard deviation averaged from duplicate experiments. The results show that dexamethasone is effective over concentrations ranging from $10^{-5}$ to $10^{-11}$ in potentiating the mitogenic activities of PDGF or PDGF in combination with IGF-1 (FIG. 2). The concentration of dexamethasone to potentiate optimally the mitogenic activity of PDGF at 200 mg/ml is estimated to be $10^{-7}$M. In addition, the ability of dexamethasone in combination with PDGF alone or PDGF+IGF-1 to promote the proliferation of cells is significantly greater than that by PDGF+IGF-1 alone. However, there is no further enhancement of mitogenic activities by the addition of IGF-1 to PDGF and dexamethasone.

EXAMPLE 2

Figure 3B:
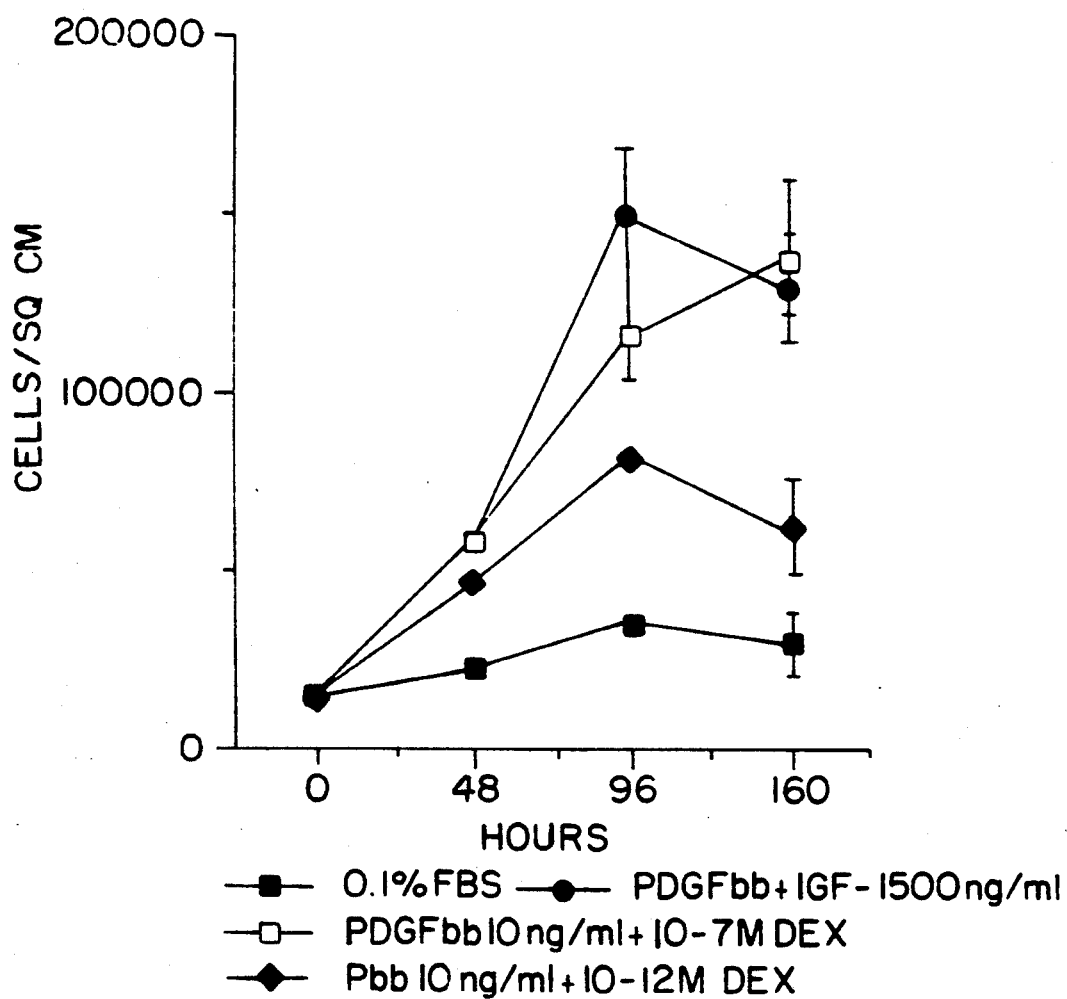

To determine the time course of the effects of dexamethasone on PDGF-$\beta\beta$ mitogenic activity, cultures were treated with PDGF+IGF-1 and PDGF with and without dexamethasone at $10^{-7}$ and $10^{-12}$M, harvested and counted at the time indicated over a period of 160 hours. The results of one representative trial of three replicate experiments are depicted in FIGS. 3A and 3B. Data from the same experiment are plotted against the controls in two separate plots for clarity.

The data reveal that a single 160 hour exposure of the cultured cells at time zero to PDGF-$\beta\beta$ plus dexamethasone results in final increased cell population densities that is similar to that obtained by exposure of the cultured cells to PDGF-$\beta\beta$ plus IGF-1. The final total cell number was similar for treatment with 10 ng/ml and 500 ng/ml PDGF-$\beta\beta$. It is worth noting that the PDGF-$\beta\beta$+IGF-1 treated cultures reached maximal cell population densities at 96 hours, while those exposed to PDGF-$\beta\beta$+dexamethasone may not have plateaued by 160 hours, indicating the prolonged effect of a single dose of PDGF+dexamethasone on cell proliferation.

EXAMPLE 3

Comparison of the Mitogenic Activity of PDGF-$\alpha\alpha$ and PDGF-$\beta\beta$.

Plates prepared as described above were treated with the following materials and the extent of cell growth determined.

PDGF-$\beta\beta$ Studies

Plate 1 contained 0.1% FBS+dexamethasone $10^{-7}$.
Plate 2 contained PDGF-$\beta\beta$ 500 ng/ml.
Plate 3 contained PDGF-$\beta\beta$ 500 ng/ml+IGF-1 500 ng/ml.
Plate 4 contained PDGF-$\beta\beta$ 500 ng/ml+$10^{-5}$M dexamethasone.

PDGF-$\alpha\alpha$ Studies

Plate 5 contained 0.1% FBS+$10^{-7}$M dexamethasone.
Plate 6 contained PDGF-$\alpha\alpha$ 500 ng/ml.
Plate 7 contained PDGF-$\alpha\alpha$ 500 ng/ml+IGF-1 500 ng/ml.
Plate 8 contained PDGF-$\alpha\alpha$ 500 ng/ml+$10^{-7}$M dexamethasone.

Figure 4A:
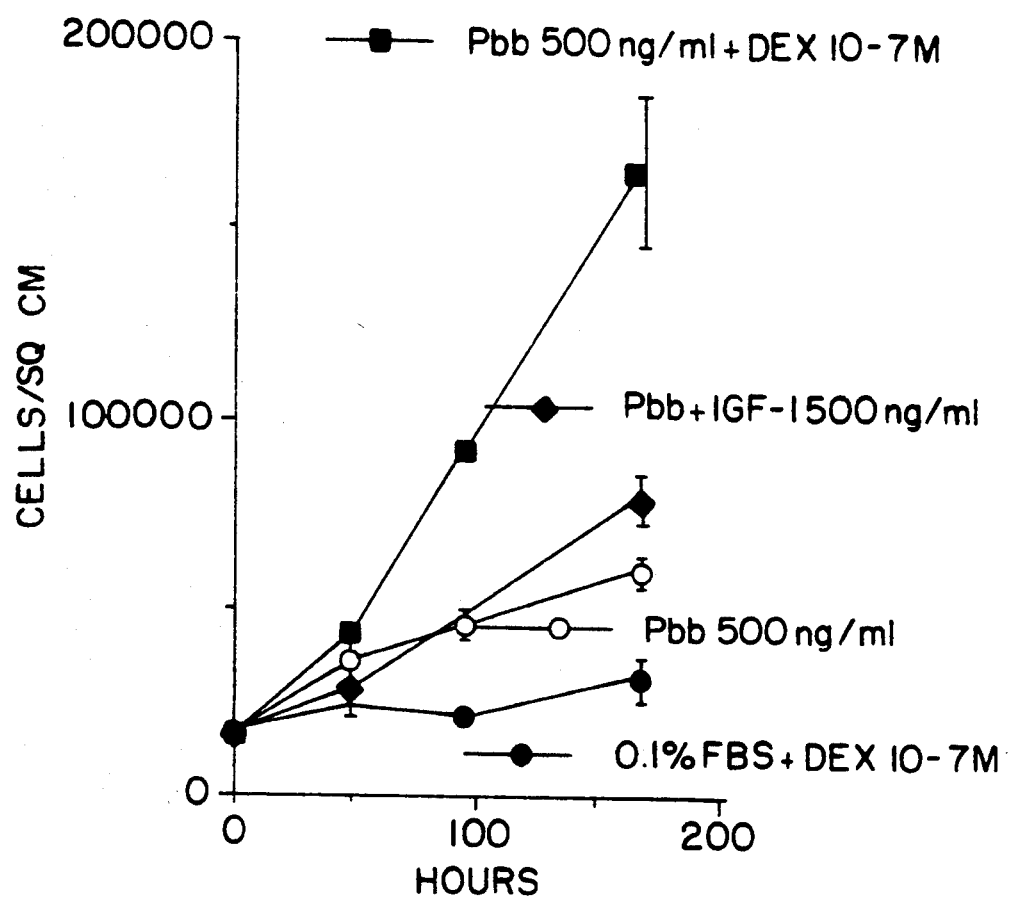
FIGS. 4A and 4B graphically illustrates the data from Example 3 comparing the mitogenic activity of PDGF-$\alpha\alpha$ with the mitogenic activity of PDGF-$\beta\beta$
Figure 4B:
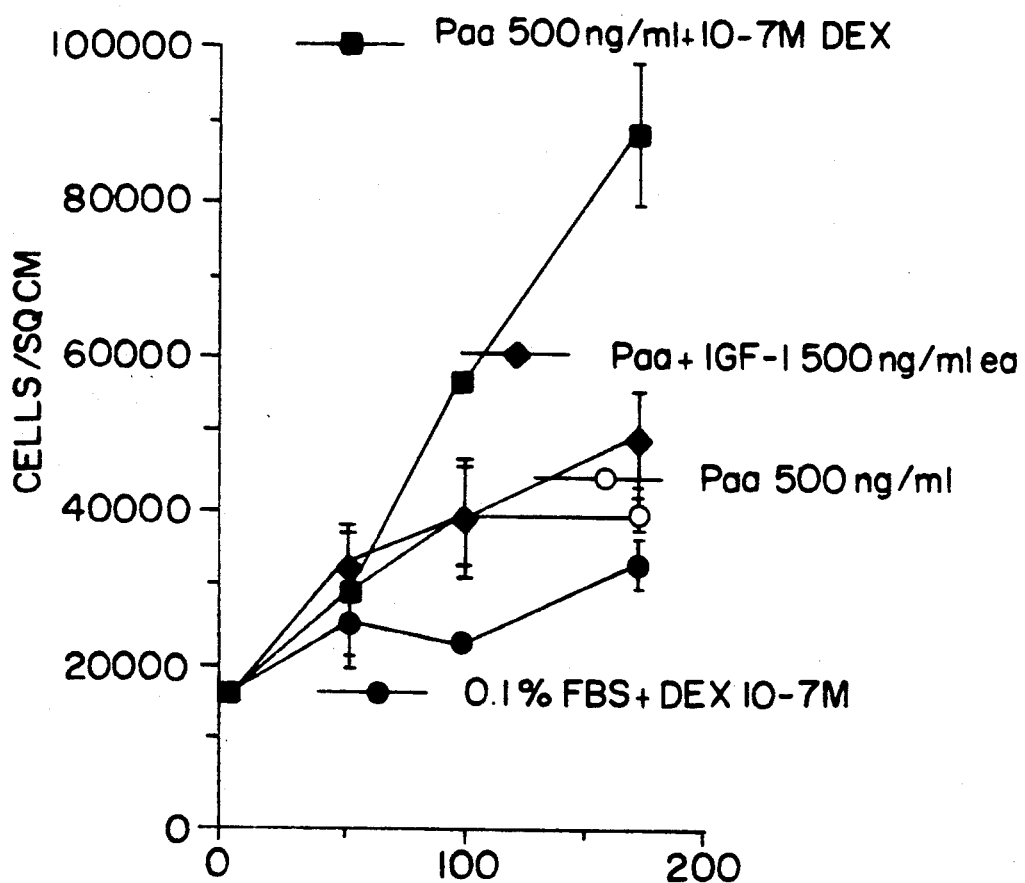

The results of the present experiment are shown in FIGS. 4A and 4B which demonstrates that dexamethasone potentiates the mitogenic activity of PDGF-$\alpha\alpha$ and PDGF-$\beta\beta$. As indicated above, after a single application of PDGF plus dexamethasone the rate of cell proliferation at 168 hours does not appear to have diminished. The data (Table 1) suggests that PDGF-$\beta\beta$ is a more potent mitogen than PDGF-$\beta\beta$, and that PDGF-$\alpha\alpha$ treated cultures may be slightly more responsive to dexamethasone than PDGF-$\alpha\alpha$ treated cultures (Table 1).

TABLE 1

| PDGF-$\beta\beta$ DEX/ PDGF-$\beta\beta$ | PDGF-$\alpha\alpha$ DEX + PDGF-$\alpha\alpha$ | PDGF-$\beta\beta$ + PDGF-$\alpha\alpha$ |
|---|---|---|
| 48 HOURS 1.24 | 0.92 | 1.08 |
| 96 HOURS 1.97 | 1.44 | 1.32 |
| 168 HOURS 2.73 | 2.19 | 1.57 |

Data are ratios of means of cells/cm² from replicate experiments.

What is claimed is:

1. A method for promoting regeneration and repair of dental tissue in a mammal comprising:
    applying to said tissue a therapeutically effective amount of a composition comprising platelet-derived growth factor (PDGF) and dexamethasone.

2. The method of claim 1, wherein the tissue is epithelium.

3. The method of claim 1, wherein the tissue is cartilage or bone.

4. The method of claim 1 wherein the composition of PDGF and dexamethasone further comprises a pharmaceutically acceptable carrier.

5. The method of claim 4, wherein the pharmaceutically acceptable carrier is selected from a group consisting of creams, ointments, gels and collagen matrix.

6. A method for promoting healing of an external wound in the dental tissue of a mammal comprising:
applying to said external wound a therapeutically effective amount of a composition comprised of platelet-derived growth factor (PDGF) and dexamethasone.

7. The method of claim 6, wherein the tissue is epithelium.

8. A method for regenerating dental bone or cartilage tissue of a mammal comprising:
applying to said dental cartilage or bone a therapeutically effective amount of a composition of platelet-derived growth factor (PDGF) and dexamethasone.

9. A method for treating gum disease or periodontal ligament afflicted with periodontal disease comprising:
applying to the gum tissue or periodontal ligament a therapeutically effective amount of a composition comprising platelet-derived growth factor (PDGF) and dexamethasone.

10. The method of claim 9, further comprising a pharmaceutically acceptable carrier.

11. The method of claim 10 wherein the pharmaceutically acceptable carrier is selected from the consisting of creams, ointments, gels and collagen matrix.

* * * * *

UNITED STATES PATENT AND TRADEMARK OFFICE
CERTIFICATE OF CORRECTION

PATENT NO. : 5,149,691

DATED : September 22, 1992

INVENTOR(S) : Robert B. Rutherford

It is certified that error appears in the above-identified patent and that said Letters Patent is hereby corrected as shown below:

Title page, items [57], [75] and [73] should read as follows:

[54] Tissue Repair and Regeneration Through the Use of Platelet Derived Growth Factor (PDGF) in Combination With Dexamethasone

[75] Inventor: Robert B. Rutherford, Farmington, Conn. and Marc F. Charette, Needham, Mass.

[73] Assignee: Creative BioMolecules, Inc., Hopkinton, Mass. and University of Connecticut, Storrs, Conn.

Col. 1, line 1, change "ISSUE" to --TISSUE--.
Col. 1, line 38, change first occurence of "of" to --at--.
Col. 1, line 59, delete "that".
Col. 2, line 51, delete "in a small 1".

Signed and Sealed this

Twenty-sixth Day of January, 1993

Attest:

STEPHEN G. KUNIN

Attesting Officer

Acting Commissioner of Patents and Trademarks